(12) United States Patent
Getin et al.

(10) Patent No.: US 7,366,377 B2
(45) Date of Patent: Apr. 29, 2008

(54) PARTICLE CONCENTRATION METHOD

(75) Inventors: Stephane Getin, Grenoble (FR); Alexandra Fuchs, Beaulieu (FR); Guillaume Colas, Grenoble (FR); Stephanie Gaugiran, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/581,483

(22) PCT Filed: Dec. 3, 2004

(86) PCT No.: PCT/EP2004/053262

§ 371 (c)(1),
(2), (4) Date: Jun. 2, 2006

(87) PCT Pub. No.: WO2005/054819

PCT Pub. Date: Jun. 16, 2005

(65) Prior Publication Data

US 2007/0086701 A1    Apr. 19, 2007

(30) Foreign Application Priority Data

Dec. 4, 2003 (FR) ................... 03 50973

(51) Int. Cl.
  G02B 6/12  (2006.01)
  G02B 6/34  (2006.01)
  G01N 15/14 (2006.01)
  G21K 1/00  (2006.01)

(52) U.S. Cl. ............... 385/37; 385/15; 250/251

(58) Field of Classification Search ............ None
See application file for complete search history.

(56) References Cited

U.S. PATENT DOCUMENTS

| 4,945,050 | A  | * | 7/1990  | Sanford et al. ........... 435/459 |
| 5,858,192 | A  |   | 1/1999  | Becker |
| 5,888,370 | A  |   | 3/1999  | Becker |
| 5,993,630 | A  |   | 11/1999 | Becker |
| 5,993,632 | A  |   | 11/1999 | Becker |
| 6,833,542 | B2 | * | 12/2004 | Wang et al. ........... 250/251 |
| 7,068,874 | B2 | * | 6/2006  | Wang et al. ........... 385/16 |
| 7,211,787 | B2 | * | 5/2007  | Gaugiran et al. ........ 250/251 |
| 2003/0111594 | A1 | * | 6/2003 | Getin et al. ........... 250/251 |

FOREIGN PATENT DOCUMENTS

| DE | 19860118 | 9/2000 |
| EP | 1 324 645 | 7/2003 |
| WO | 0000292 | 1/2000 |

(Continued)

OTHER PUBLICATIONS

U.S. Appl. No. 10/581,199, filed Jun. 1, 2006, Getin et al.

(Continued)

Primary Examiner—Michelle Connelly-Cushwa
Assistant Examiner—Omar Rojas
(74) Attorney, Agent, or Firm—Oblon, Spivak, McClelland, Maier & Neustadt, P.C.

(57) ABSTRACT

A method for concentrating particles, including: placing the particles close to and/or on at least one waveguide of a support, and injecting light radiation into the waveguide causing grouping of particles into one or plural clusters on the waveguides.

20 Claims, 9 Drawing Sheets

FOREIGN PATENT DOCUMENTS

| | | |
|---|---|---|
| WO | 00 37920 | 6/2000 |
| WO | 00 69565 | 11/2000 |

OTHER PUBLICATIONS

U.S. Appl. No. 10/581,483, filed Jun. 2, 2006, Getin et al.
U.S. Appl. No. 10/581,484, filed Jun. 2, 2006, Getin et al.
Tanaka, Takuo et al.,"Optically Induced Meandering Mie Particles Driven by the Beat of Coupled Guided Modes Produced in a Multimode Waveguide", Japanese Journal of Applied Physics 2, vol. 41, No. 3A, pp. L260-L262, 2002.
Zharov, Vadimir,"Photoacoustic Tweezers", Optical Diagnostics of Living Cells V, Proceedings of SPIE, vol. 4622, pp. 143-153, 2002.
Kawata, S. et al.,"Optically Driven Mie Particles in a Evanescent Field Along a Channeled Waveguide", Optics Letters, vol. 21, No. 21, pp. 1768-1770, 1996.

Kawata, Satoshi et al.,"Movement of Micrometer-Sized Particles in the Evanescent Field of a Laser Beam", Optics Letters, vol. 17, No. 11, pp. 772-774, 1992.
Ashkin, A, et al."Observation of Radiation-Pressure Trapping of Particles by Alternating Light Beams" Physical Review Letters, vol. 54, No. 12, pp. 1245-1248, 1985.
Ng, L.N. et al.,"Propulsion of Gold Nanoparticles on Optical Waveguides", Optics Communications, vol. 208, No. 1-3, pp. 117-124, 2002.
Ng, L.N. et al.,"Manipulation of Colloidal Gold Nanoparticles in the Evanescent Field of a Channel Waveguide", Applied Physics Letters, vol. 76, No. 15, pp. 1993-1995, 2000.

* cited by examiner

PARTICLE CONCENTRATION METHOD

TECHNICAL DOMAIN AND PRIOR ART

This invention relates to the domain of treatment and particularly concentration of small particles. These particles may be biological particles such as liposomes, animal or vegetable cells, viruses or micro-organisms, macromolecules, for example such as DNA, RNA or proteins, or inorganic particles such as microballs. Application domains may then be chemical or biomedical analysis or quality control (calibration of micro-particles).

Known approaches in terms of particle cell sorting, such as flow cytometry, reach their limits particularly for the analysis of rare or very minority cell populations.

The technique of optical clamps is based on the confinement of a particle (microball, or cell or macromolecule) by the intensity gradient generated at the waist of a continuous laser beam. For example, it is described in the article by "Ashkin and Dziedic" entitled "Observation of radiation-pressure trapping of particles by alternating light beams" published in Physics Review Letters, 54(12), 1985. This operation is made possible by balancing of radiation pressures. Once this operation has been done, the particle is displaced by displacing the beam.

Thus, displacement distances on this type of device are usually limited to a few hundred microns.

Finally, treatment and particularly concentration of particles is not possible.

Figure 1:
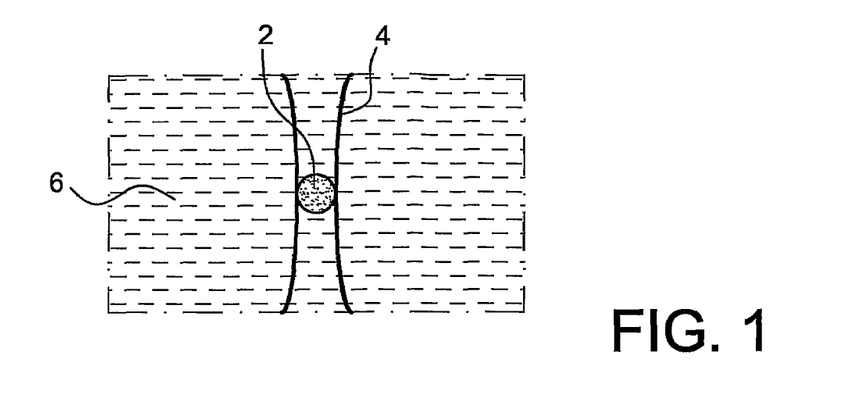
FIGS. 1, 2 and 3 illustrate techniques according to prior art.

FIG. 1 shows the principle of such a device.

A particle 2 is confined by a beam 4 in a liquid medium 6.

Figure 2:
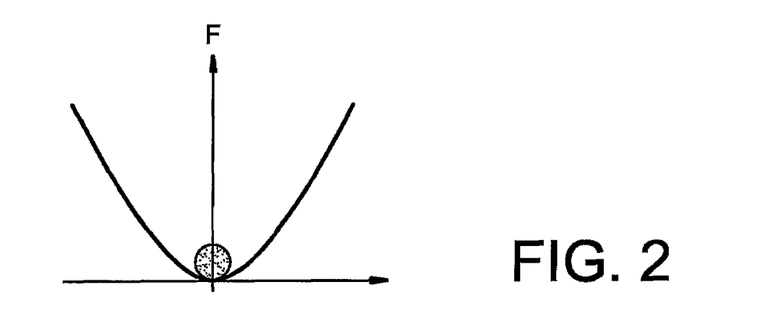

FIG. 2 is a diagram showing a force field generated by the device, on each side of the laser beam 4; the particle is confined in a mechanical force field (induced by the radiation pressure provoked by the electrical field of the laser) which makes it possible to trap it.

This type of device has a disadvantage: displacement of particles is based on use of a dedicated mechanical system, which may be difficult and expensive to set up.

Recent work, for example such as that described in the article by T. Tanaka et al, published in Applied Physics Letters, Vol. 77, p. 3131, 2000, makes use of guided optical devices, and suggests the possibility of designing a device for displacement of cells by optical forces; this technique is limited to objects very much smaller than a biological cell (balls and colloids with a size of the order of a few microns).

Figure 3:
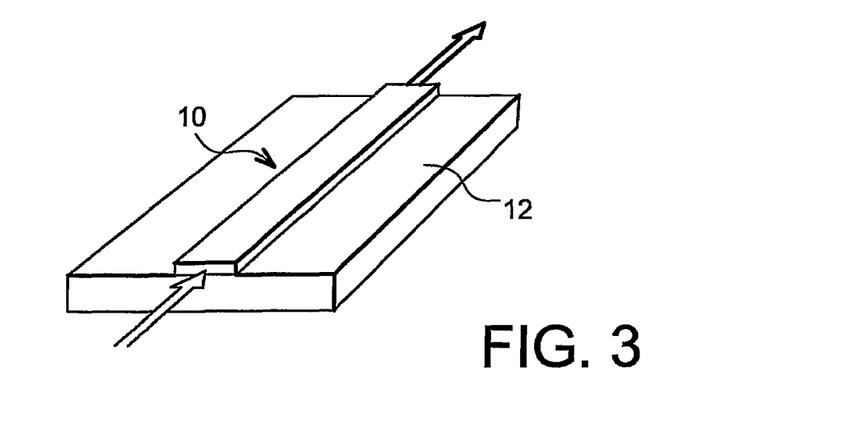

As illustrated in FIG. 3, this device uses a waveguide 10 with a strip made on a substrate 12. A particle is displaced by a force with photonic pressure, which is proportional to the light intensity at the particle. The particle is held in place in the guide by a force that is proportional to the gradient of the intensity.

If the waveguide is single mode, there is a maximum light intensity at the location at which the particle will be trapped.

Furthermore, if it is desired to concentrate objects such as biological cells, special care must be taken not to damage them. Concentration methods involving liquid flows (for example concentration by retention on a membrane) cause the problem of a possible overpressure that is highly damaging to cells and that can occur following a blocking in the guide circuit.

The use of optical clamps, although less damaging for cells, is also not feasible since each clamp can only handle a single object and in this case it will be necessary to make one manipulation for every particle to be displaced. This method is fairly tedious and requires qualified personnel and/or very delicate computer control.

The problem arises of finding a method and a device for concentrating particles simply and efficiently.

PRESENTATION OF THE INVENTION

The invention relates to systems for concentrating particles or objects, for example with biological interest.

The invention uses at least one waveguide, for example with a length between a few micrometers and a few centimetres.

Particles may then be concentrated in one or several clusters: the particles to be concentrated are firstly placed close to a portion of the guide. Light radiation is then injected into the waveguide which produces forces that attract all particles and concentrate these particles in a cluster.

In particular, these forces may be short range optical forces (of the order of a few micrometers and/or forces related to convection of a fluid above the guide, which have a longer range (several tens of micrometers).

The invention may also use several waveguides so that particles can be concentrated in one or several clusters. These clusters may be distributed on one or several guides, or possibly on each of the waveguides. According to one variant, this can be achieved by adding light radiation into each of the waveguides, during the step in which light radiation is inserted. According to another variant, light radiation can be inserted into one or several particular guides among the set of waveguides.

The said waveguides may be put adjacent on a support without intersecting. They may also be multiplexed and joined together at least at one concentration point. In this case, the injection step can be used to concentrate the particles into a single cluster on this concentration point.

Once concentrated on one or several waveguides, the particles may tend to displace; the particle cluster(s) formed may then tend to dislocate.

According to one characteristic of the invention, stationary waves may be used to prevent this displacement. These stationary waves may be formed from the light radiation used, for example using a diffraction grating or an optical loop formed by the waveguide.

The use of stationary waves may also help to hold particles concentrated in several clusters fixed on the same waveguide.

The said injected light radiation may be between the ultraviolet and infrared. It is chosen particularly according to criteria such as the nature of the particles to be concentrated, and the velocity at which this concentration has to be done.

The particles to be concentrated may be objects derived from a micro-manufacturing method for example such as microballs with a size between a few nanometres and about a hundred micrometers. These particles may also for example be biological elements such as cells, macromolecules such a proteins, DNA, RNA.

According to one particular characteristic of the method according to the invention, the particles to be concentrated may be marked before being placed on the said support used. This provides means for increasing the difference in the index of particles with respect to their environment and can thus improve their concentration when light radiation is injected.

For example, when the particles to be concentrated are cells, marking may be done by other marking particles, for example based on metal such as gold or polymer. These marking particles may for example be microballs.

The method according to the invention may be done in a liquid medium such as water or a buffer solution, or a cell suspension medium.

The method may be carried out in such a medium particularly when the particles to be sorted are biological elements.

The invention also relates to a particle concentration device including one or several waveguides, the waveguides being surrounded on each side by at least two diffraction gratings.

BRIEF DESCRIPTION OF THE FIGURES

This invention will be better understood after reading the description of example embodiments given purely for information purposes and in no way limitative, with reference to the appended figures wherein.

Identical, similar or equivalent parts of the different figures are marked with the same numeric references so as to facilitate comparison between one figure and the others.

The different parts shown in the figures are not necessarily at the same scale, to make the figures more easily readable.

DETAILED PRESENTATION OF PARTICULAR EMBODIMENTS

A general example of the method according to this invention will now be described with reference to FIGS. 4A and 4B.

This method is used to concentrate or to group a set of particles 100. Grouping may be done so as to form one or several particle clusters.

Particles mean organic or inorganic elements or objects with a size varying from 5 nanometres to 100 micrometers. These particles may for example be biological elements such as liposomes, viruses, micro-organisms, animal or vegetable cells, macromolecules for example such as proteins, DNA, RNA or micro-objects, for example such as microballs based on a metal or a dielectric material.

The concentration method according to the invention is done on a support 104, for example made of glass or silicon, with an optical index preferably different from or very different from the optical index of the particles that are to be grouped. This support 104 comprises at least one integrated multi-mode or single mode waveguide 108 for example with a length of between a few micrometers and a few centimetres.

According to a first step in the method, the particles 100 are placed firstly in an area 102 close to and/or on the waveguide 108, using a manual or automated method.

Then, using an optical device 112 that may or may not be integrated into the support 104, light radiation R is injected into the optical guide. The injected radiation has a wavelength between the near ultraviolet and infrared, for example between 300 nm and 1200 nm (FIG. 4A).

The light radiation R may be chosen particularly depending on the type of particles to be concentrated, and possibly the velocity at which these particles are to be grouped.

For example, in the case in which the particles are biological elements such as cells, a wavelength between the red and infrared could be used, for example using a YAG laser with a wavelength of 1064 nm. The radiation power could be of the order of a few tens of milliwatts to a few hundred milliwatts, for example between 50 mW and 1 W, for example close to 150 mW.

The light radiation R through the waveguide 108 creates forces $\vec{f}$ towards the waveguide. These forces may attract and concentrate particles 100 on the waveguide 108. These particles 100 then form a cluster 106 (FIG. 4B).

The velocity at which the particles are grouped can vary depending on the mass, the volume, optical index of the particles, and the wavelength of the light radiation used.

If the light radiation injection step is prolonged, the cluster 106 may tend to be dislocated. Particles can tend to displace along the waveguide 108 along the direction of propagation of light radiation.

If it is required to prevent this phenomenon, according to one variant, the injection of light radiation can be stopped as soon as the cluster 106 of particles 100 is formed.

According to another variant, the particles 100 can be blocked once they are on the waveguide, for example using stationary waves. These stationary waves may be formed by transforming the light radiation R in the waveguide, for example using one or several diffraction gratings, or by making an optical loop system.

Figure 4A:
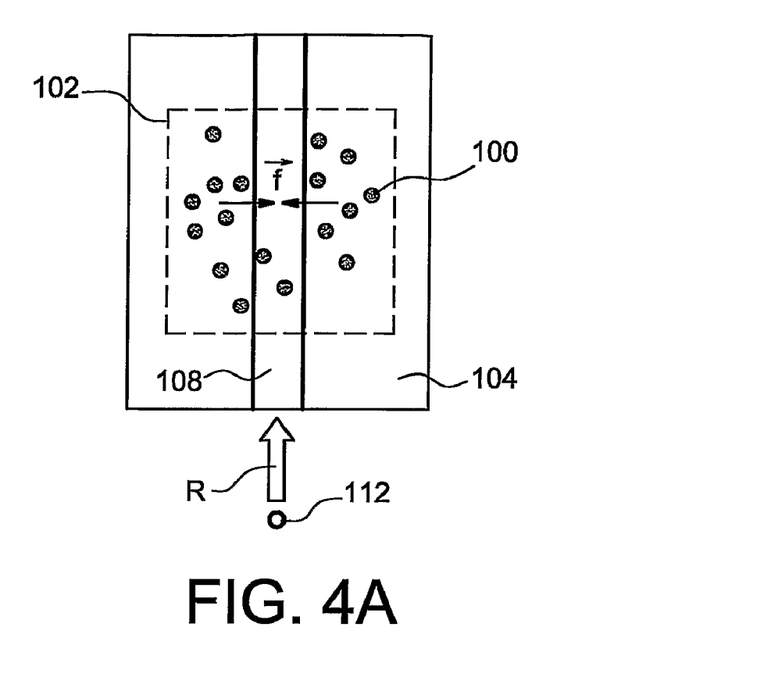
FIGS. 4A and 4B illustrate a general example of a method for concentration of particles according to the invention.
Figure 4B:
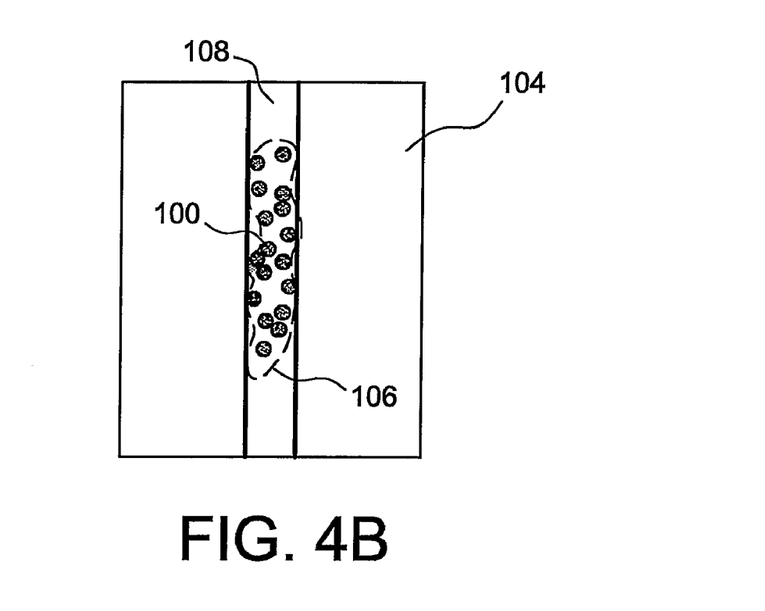
Figure 5A:
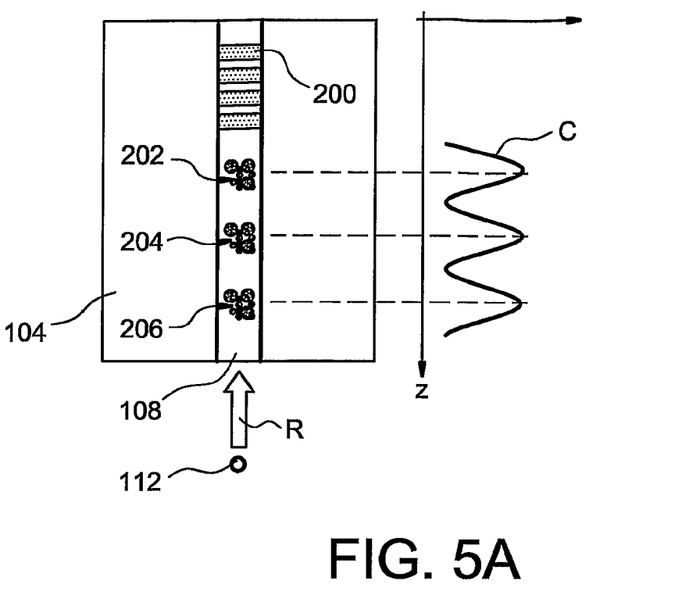
FIGS. 5A and 5B illustrate examples of devices for concentrating particles into one or several stationary clusters on the same waveguide.

FIG. 5A relates to a device like the one illustrated in FIGS. 4A and 4B. The waveguide 108 also comprises an integrated diffraction grating 200 used to transform light radiation produced by the optical device 112 into stationary waves.

The use of stationary waves through waveguide 108 can also concentrate and maintain particles in several clusters 202, 204, 206 formed along the same guide 108.

These clusters 202, 204, 206 are located at locations on the waveguide at which the light intensity is maximum.

The curve C illustrated in FIG. 5A represents the variation in the amplitude of a stationary wave derived from the radiation R, along a z axis transverse to the waveguide and along the direction of propagation of the radiation R. The maximum values of the curve C correspond to the locations on the waveguide 108 at which particle clusters are grouped.

Figure 5B:
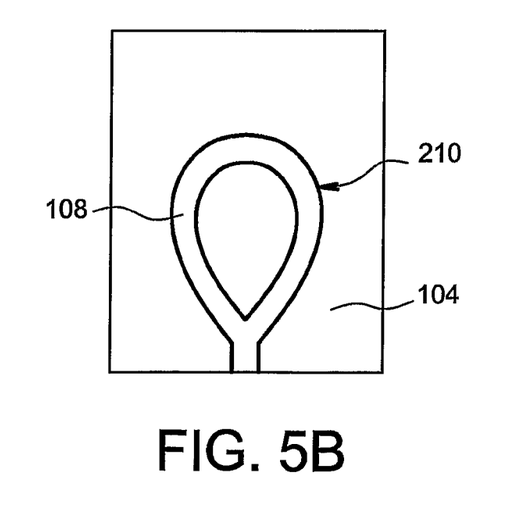

According to one variant, a stationary wave can be made in the waveguide using a guide forming at least one loop 210 like that illustrated in FIG. 5B. This type of loop can enable light radiation, when it passes along the waveguide, to adopt one or two different trajectories. Thus, two light waves with the same length and the same amplitude propagating in different directions, can come into contact and interfere.

The method for concentration of particles according to the invention may also be used with a device comprising several waveguides. It is required to concentrate a group of particles placed in an area close to the different waveguides into one or several clusters using such a device.

For example, this variant may be produced using a support comprising several adjacent waveguides with certain spacing between them. These waveguides may have different lengths and/or different widths and may be made of different materials.

A first method of grouping particles consists of injecting light radiation into one of the waveguides. If the distance between the different adjacent waveguides is small enough, coupling between the guides can occur and the light radiation then propagates in one or more of the other guides. When coupling occurs, the particles may be attracted by forces from the different guides and may be concentrated in different clusters distributed on these different guides.

However, when coupling occurs between several guides, it is possible that a particle oscillation phenomenon can occur from one waveguide to another. Another phenomenon can also occur in which particles remain blocked between two waveguides.

In order to optimise the concentration method and prevent these two phenomena, the distance between the waveguides may be fixed equal to a value greater than a minimum distance that will enable coupling between the different guides. However, this minimum distance depends particularly on the geometric properties of the guide, the refraction index of the materials from which it is made, and the wavelength of the radiation used. It may be of the order of a few micrometers, for example more than 5 µm, to several tens of micrometers, for example between 5 µm and 50 µm.

Figure 6A:
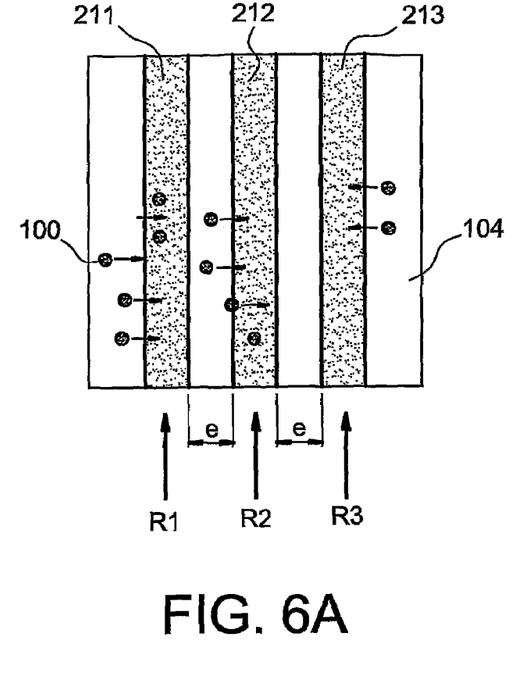
FIGS. 6A and 6B illustrate an example of the method for concentration of particles according to the invention in which several adjacent waveguides are used.
Figure 6B:
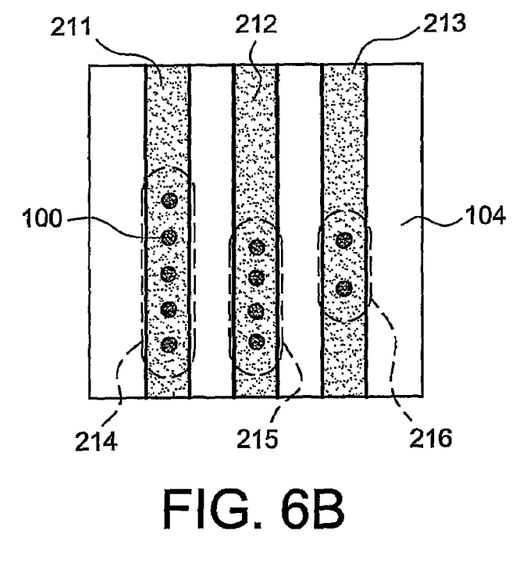

An example of a device comprising several adjacent waveguides 211, 212, 213 at a spacing of a distance e, is illustrated in FIG. 6A. The distance e is fixed so as to avoid coupling between the different waveguides, at a value for example of the order of one or several tens of micrometers, for example 10 or 20 µm. Different light radiation $R_1$, $R_2$, $R_3$ can be injected into each of the waveguides 211, 212, 213, to concentrate the particles 100 located close to the waveguides 211, 212, 213 (FIG. 6A). This provides a means of concentrating the particles 100 into different clusters 214, 215, 216 distributed on the different waveguides (FIG. 6B).

At the end of this method, it will be possible to group the different particle clusters distributed on several waveguides into a single cluster.

Figure 7:
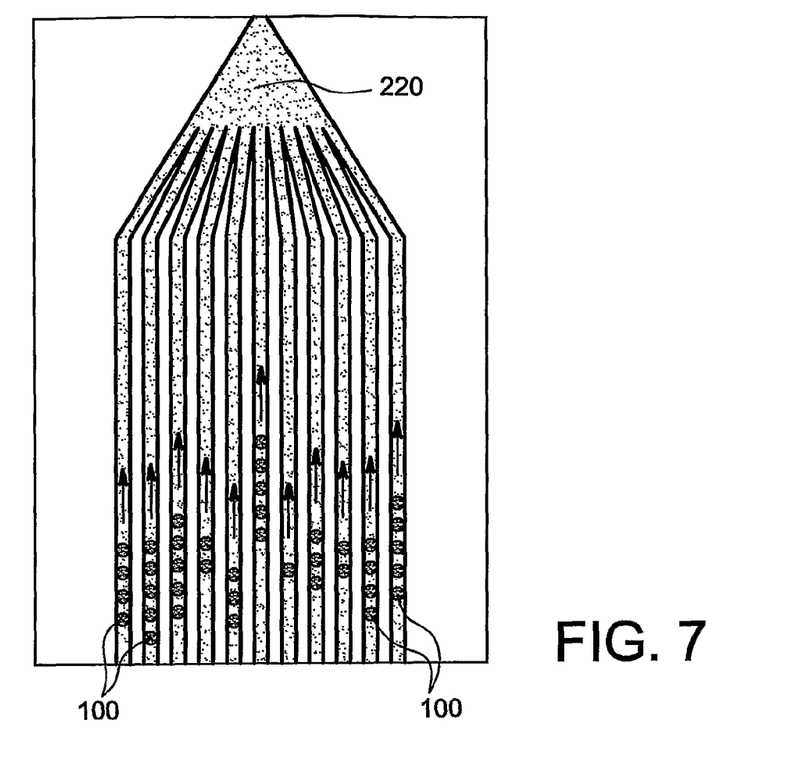
FIG. 7 illustrates an example of a device for grouping several clusters of particles distributed on different waveguides, into a single particle cluster.

To achieve this, a support 104 can be used including several adjacent and multiplexed waveguides. These guides join together at a concentration point 220 (FIG. 7). The injection of light radiation through each of the waveguides causes concentration of particles into several clusters distributed on the different waveguides. Then, if the emission of light radiation is prolonged, the particles 100 tend to displace along radiation propagation directions (indicated by the arrows in FIG. 4). The particles 100 then move towards the concentration point. The particles 100 are concentrated in a single cluster.

Figure 8:
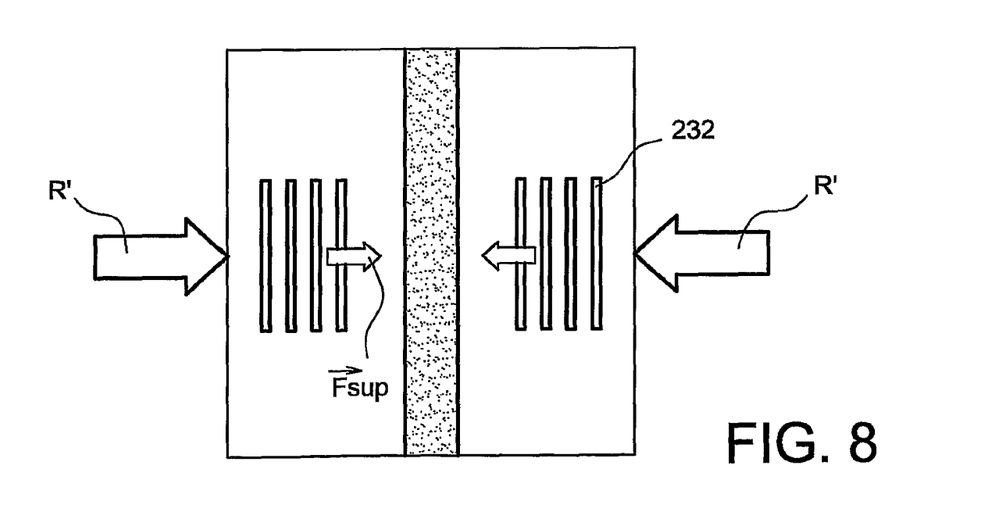
FIG. 8 illustrates an example device used to facilitate concentration of particles on a waveguide.

One method of improving the concentration of particles consists of producing additional radiation forces $\vec{F}_{add}$ on the particles 100, added to forces created by the waveguide. These additional radiation forces $\vec{F}_{add}$ may for example be produced by diffraction gratings 232 located on each side of the waveguide through which additional light radiation R' is injected (FIG. 8).

The method according to this invention may be applicable to biological particles such as animal or vegetable cells to be concentrated. A support, for example made of glass, comprising at least one waveguide will be used to concentrate biological particles.

The support may be immersed in a liquid solution, preferably biocompatible, to preserve cells.

In a heterogeneous cell sample, an attempt is made to isolate a given sub-population characterised by a specific phenotype, for example the presence of a certain type of surface macromolecules, for example such as proteins. Furthermore, probe molecules such as antibodies are available capable of recognising and bonding with these phenotypic markers with a very strong affinity. In the case of antibody type probe molecules, the phenotypic markers are called antigens. Antibodies are fixed by means known to those skilled in the art to balls chosen for their particular characteristics, for example gold balls. These functionalised gold balls are then grafted onto the surface of cells, for example these cells may be lymphocytes isolated from blood and that are to be concentrated.

A group of marked cells is sampled firstly, for example, using a pipette. The next step is to place the said sample in a support receptacle. This receptacle may be a chamber, for example such a Gene Frame® type chamber. This self-sticking chamber is very simple and has a joint system impermeable to gas, providing resistance at high temperatures. The receptacle is not limited to this type of chamber.

The cells group may be transferred from the receptacle to a zone placed close to the waveguide, for example one or several capillaries.

The next step is to inject light radiation through said waveguide. The radiation used during a cell sort would preferably be inoffensive towards the cells. Thus, the light radiation used may be laser radiation emitting at a wavelength between far red and near infrared, for example between 1000 nm and 1200 nm, for example close to 1064 nm.

The passage of laser radiation through the waveguide creates forces directed towards the guide to attract the cells. The cells are then concentrated into a cluster.

In general, observation means may be provided, for example a CCD camera located above the guide 108. These means enable monitoring of the sort made as described above.

Figure 9:
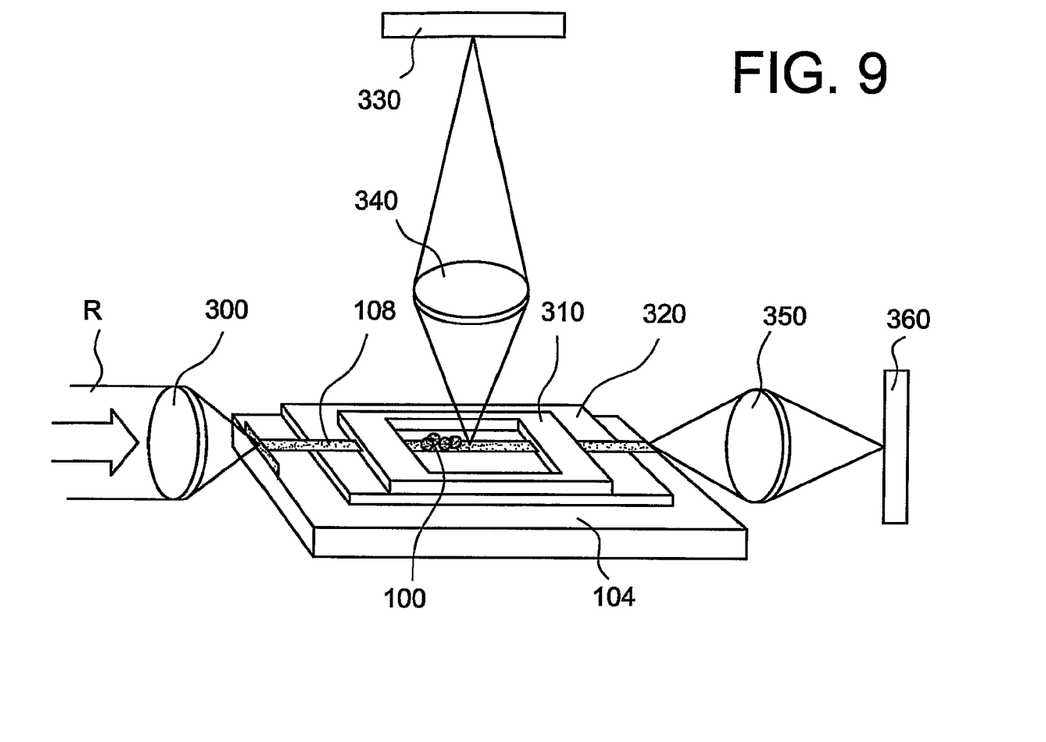
FIG. 9 illustrates an example device used to observe the concentration of particles on a waveguide.

FIG. 9 shows a particle concentration system 100 on a support 104 incorporating a guide system according to the invention. An objective 300 focuses a laser beam R (for example a YAG beam at 1064 nm) in a guide 108. The particles to be sorted are contained in a chamber 310 located on a slide 320. A camera 330 is used to make an image of the concentration, for example using a focusing device or a zoom 340. Means 350, 360 (objective, camera) of forming an image of the transmitted radiation may also be placed at the output from the device.

A device for implementing a concentration method according to the invention like those described above, particularly including for example a support and one or several waveguides, may be integrated in a MEMS (micro-electro-mechanical system) or in a lab on a chip.

Waveguides used during the method according to the invention can for example be made by thin layer manufacturing techniques, or for example by an ion exchange method.

The support on which these guides are formed may for example be based on glass.

Figure 10A:
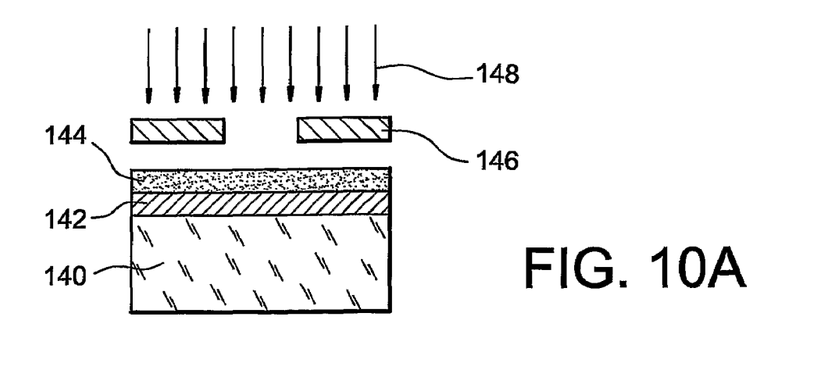
FIGS. 10A to 10D, 11 illustrate an example of a method for making waveguides that can be used during the method according to the invention.

To form the waveguide, the first step is to cover the support 140 with a metallic thin layer 142, for example based on aluminium, by a method such as evaporation or sprinkling. This aluminium layer is then covered by a resin layer 144, for example a photoresist resin layer.

To make the patterns of waveguides in the support, the first step is to expose the photoresist resin layer for example using a beam of ultraviolet rays 148 through a mask 146, for example made of chromium. The mask 146 includes a copy of the waveguide patterns or negatives of the waveguide patterns (FIG. 10A). The areas of the resin layer 144 that are not concealed by the mask have their chemical structures modified.

Figure 10B:
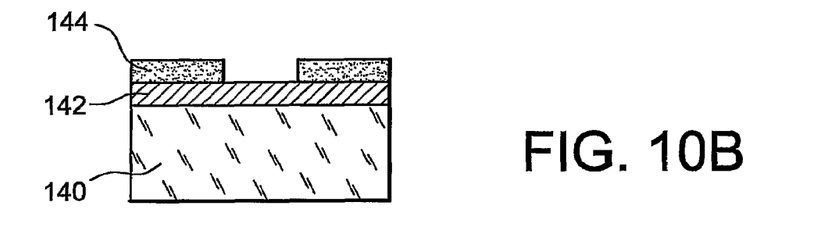

The next step after the exposure step is to develop the layer of photoresist resin 144. Thus, the areas on which the chemical structure was modified by insolation are etched (FIG. 10B).

Figure 10C:
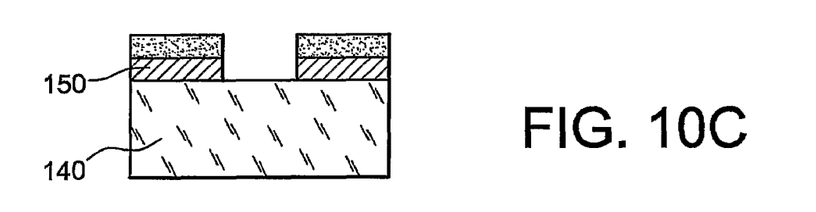

The next step is to etch the aluminium layer through the resin layer (FIG. 10C), for example by dipping the support in an aluminium etching solution (AluEtch). This solution does not etch the resin. Thus, only the previously developed parts are etched.

Figure 10D:
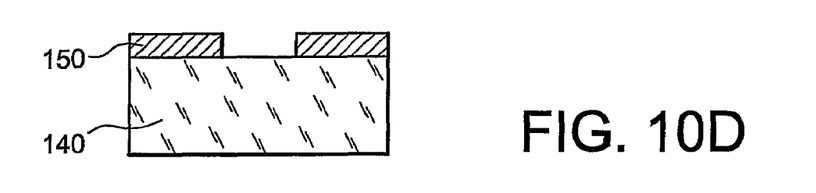

The resin layer 144 is then removed, for example using acetone (FIG. 10D).

Figure 11:
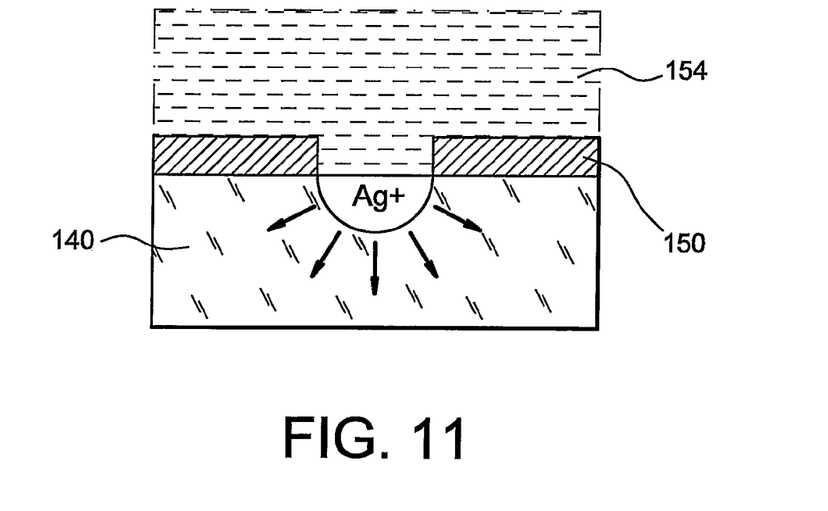
Figure 12A:
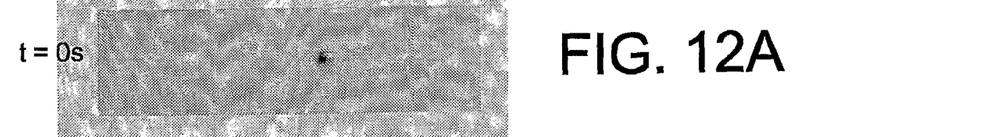
FIGS. 12A to 12D, 13, 14A to 14C show experimental results obtained using the method and a device according to the invention.
Figure 12B:
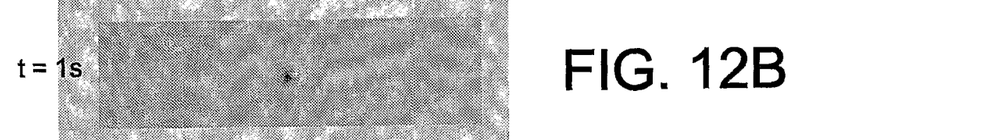
Figure 12C:
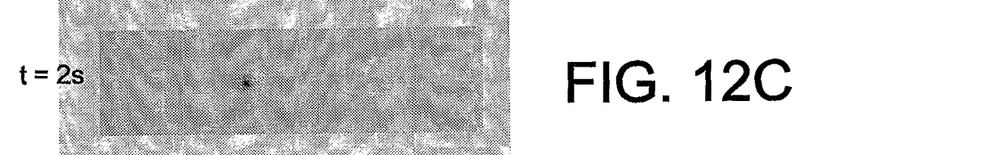
Figure 12D:
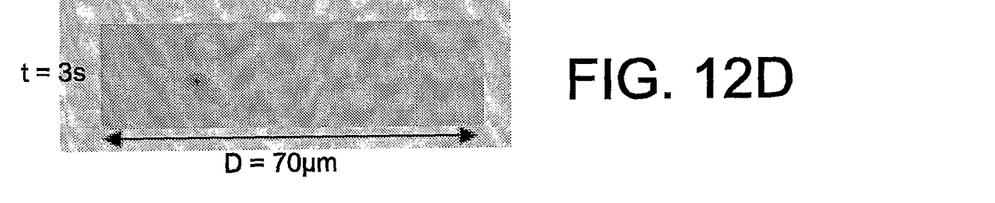

An ion exchange step is then carried out to form the waveguides. The support is then immersed in a salt bath containing silver nitrate and sodium nitrate. The proportion between these salts determines the silver content that is exchanged in the glass 140. The bath generally contains between 10% and 50% of silver depending on the application. Since the salt melting temperature is about 310° C., the exchange step is carried out at between 320° C. and 350° C. (FIG. 11).

The aluminium layer is then removed by etching. Annealing can possibly be done; the glass plate is heated without any contact with a bath. This step enables silver ions to penetrate more deeply towards the inside of the support.

A guide 104 like that illustrated in FIG. 1A can be formed in this way.

Other methods can also be used, for example to make a guide on a silicon substrate.

Braking forces on particles caused by friction with the upper surface of the guide can be reduced, by coating the guide with a special coating, for example a thin Teflon based layer.

Another example embodiment will be given. In this example, the waveguides used are surface guides made by a potassium ion exchange (glass slide substrate). These ions are produced at a temperature of 280° C. for an exchange time of 2 h 15. Losses of these guides are of the order of 0.2 to 0.5 dB/cm at a wavelength of 1064 nm.

The displaced particles to be concentrated are glass balls with a refraction index of 1.55 and a diameter of 2 μm, or gold balls with a diameter of 1 μm.

The device used is of the type shown in FIG. 9. Light is coupled through the edge using a continuous YAG laser at 1064 nm (P=10 W) and balls are observed through the top using a zoom system 340 coupled to a video camera 330 for monitoring their displacement.

Experiments carried out on 1 μm diameter gold balls have demonstrated spontaneous grouping of balls on the guide followed by their displacement at velocities of the order of 4 μm/s along the guide. Similarly, the possibility of grouping and displacing glass balls is demonstrated. Thus, FIGS. 12A to 14C illustrate:

FIGS. 12A to 12D; displacement of metallic particles over a distance of 70 μm, at t=0 s, 2 s, 3 s.

Figure 13:
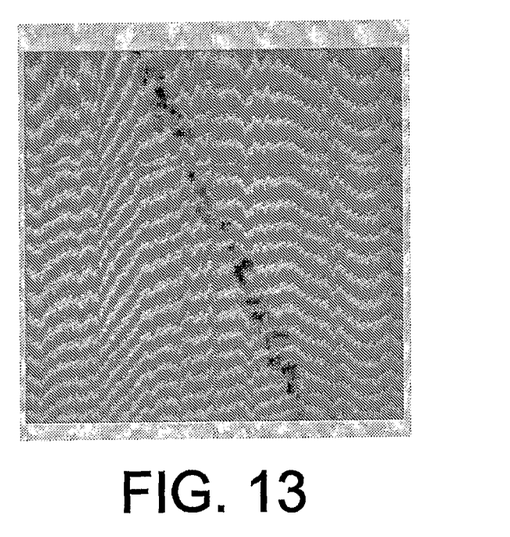

FIG. 13: a metallic particles concentration effect.

Figure 14A:
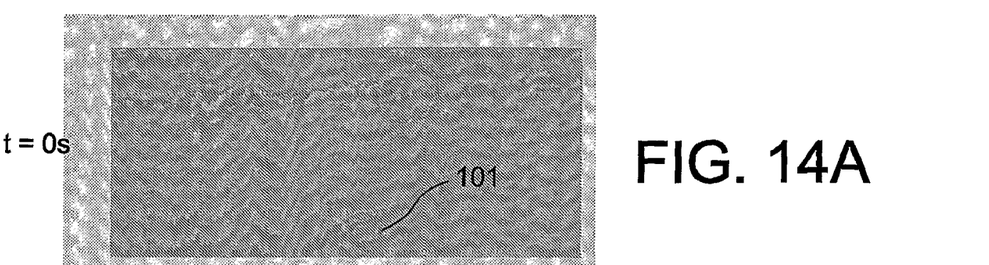
Figure 14B:
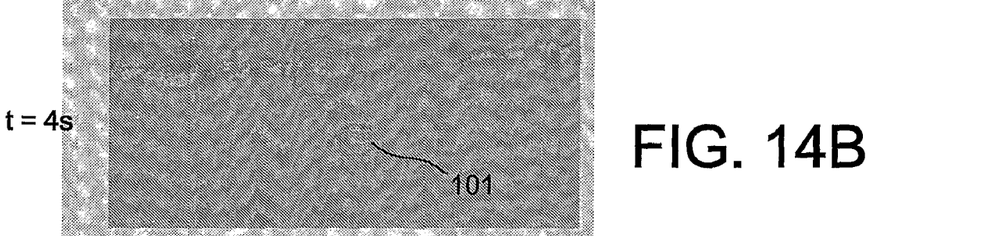
Figure 14C:
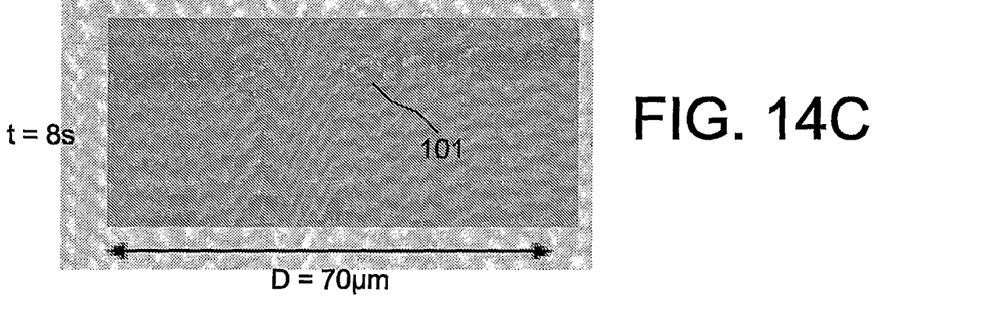

FIGS. 14A to 14C: progressive grouping of glass balls 101 along a 70 μm portion of the guide, at t=0 s, 4 s, 8 s successively.

The invention claimed is:

1. A method for concentrating particles, comprising:
   a) placing the particles close to and/or on at least one waveguide of a support;
   b) injecting, into the waveguide, light radiation forming one or more stationary waves produced through at least one diffraction grating, the injecting causing grouping of particles into one or plural clusters on the waveguide and concentrating or blocking particles into one or plural stationary clusters on a same waveguide.

2. A method for concentrating particles according to claim 1, wherein the support includes plural waveguides, and the injecting b) leads to formation of plural clusters distributed on one or plural of the waveguides.

3. A method according to claim 1, wherein the particles are cells or macromolecules or microballs.

4. A method according to claim 1, wherein the particles are glass balls and/or gold balls.

5. A method according to claim 1, wherein the radiation is in a spectral range between near ultraviolet and infrared.

6. A method according to claim 5, wherein the radiation is in a range between visible red and infrared.

7. A method according to claim 1, wherein the particles are immersed in a liquid.

8. A method according to claim 7, wherein the liquid is water.

9. A method according to claim 1, further comprising stopping injecting the light radiation as soon as a cluster is formed.

10. A method for concentrating particles, comprising:
    a) placing the particles close to and/or on at least one waveguide of a support, the waveguide forming at least one optical loop; and
    b) injecting light radiation into the waveguide, the light radiation forming one or more stationary waves, the injecting causing grouping of particles into one or plural clusters on the waveguide and concentrating or blocking particles into one or plural stationary clusters.

11. A method according to claim 10, wherein the particles are cells or macromolecules or microballs.

12. A method according to claim 10, wherein the particles are glass balls and/or gold balls.

13. A method for concentrating particles, comprising:
    a) placing the particles close to and/or on at least one waveguide of a support, the waveguide forming at least one optical loop, the waveguides being joined together in at least one concentration point; and
    b) injecting light radiation into the waveguide, the injecting causing grouping of particles into a single cluster located on the concentration point and concentrating or blocking particles into one or plural stationary clusters.

14. A method according to claim 13, wherein the particles are cells or macromolecules or microballs.

15. A method according to claim 13, wherein the particles are glass balls and/or gold balls.

16. A method according to claim 13, further comprising stopping injecting the light radiation as soon as a cluster is formed.

17. A method for concentrating particles, comprising:
    a) marking particles to modify their optical index and placing the particles close to and/or on at least one waveguide of a support;

b) injecting light radiation into the waveguide, the injecting causing grouping of particles into one or plural clusters on the waveguide; and c) concentrating or blocking particles into one or plural stationary clusters.

18. A method according to claim 17, wherein the particles are cells or macromolecules or microballs.

19. A method according to claim 17, wherein the particles are glass balls and/or gold balls.

20. A method according to claim 17, further comprising stopping injecting the light radiation as soon as a cluster is formed.

* * * * *